(12) United States Patent
Ylikorkala et al.

(10) Patent No.: US 6,569,904 B1
(45) Date of Patent: May 27, 2003

(54) AGENT FOR LOWERING ENDOTHELIN LEVELS

(75) Inventors: Olavi Ylikorkala, Helsinki (FI); Merja Metsä-Heikkilä, Järvenpää (FI); Päivi Hietanen, Espoo (FI); Juha Ellmen, Turku (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 09/857,560

(22) PCT Filed: Dec. 8, 1999

(86) PCT No.: PCT/FI99/01016

§ 371 (c)(1),
(2), (4) Date: Sep. 4, 2001

(87) PCT Pub. No.: WO96/40098

PCT Pub. Date: Dec. 19, 1996

(30) Foreign Application Priority Data

Dec. 9, 1998 (GB) .............................. 9827121

(51) Int. Cl.$^7$ ............................................ A61K 31/135
(52) U.S. Cl. ...................................................... 514/651
(58) Field of Search ......................................... 514/651

(56) References Cited

U.S. PATENT DOCUMENTS 5,595,722 A * 1/1997 Grainger et al. ............. 424/9.2
5,770,609 A * 6/1998 Grainger et al. ............. 514/319

FOREIGN PATENT DOCUMENTS

WO 9809619 * 3/1998 ......... A61K/31/135

OTHER PUBLICATIONS

Woodman, "Modulation of Vasoconstriction by Endothelium-Derived Nitric Oxide: The Influence of Vascular Disease," Clinical and Experimental Pharmacology and Physiology, vol. 22, pp. 585–595 at page 585 (1995).

* cited by examiner

Primary Examiner—James H. Reamer
(74) Attorney, Agent, or Firm—Finnegan, Henderson, Farabow, Garrett & Dunner LLP

(57) ABSTRACT

The present invention relates to a new medical use of triphenylethylene antiestrogen toremifene or a phamaceutically acceptable thereof for lowering endothelin-1 levels in mammals, and for the prevention or treatment of endothelin mediated diseases.

5 Claims, No Drawings

AGENT FOR LOWERING ENDOTHELIN LEVELS

This application is a national stage filing of PCT International Application No. PCT/FI99/01016, filed on Dec. 8, 1999, which published in the English language.

TECHNICAL FIELD OF THE INVENTION

The present invention relates to a new medical use of, and a method of treatment using, toremifene or a pharmaceutically acceptable thereof, for lowering endothelin-1 levels in mammals, and for the prevention or treatment of endothelin mediated diseases.

BACKGROUND OF THE INVENTION

Endothelin-1 (ET-1) is a 21 amino acid peptide produced by endothelial cells in response to a variety of chemical and mechanical signals. It has a powerful vasoconstrictor and bronchoconstrictor activity and exerts multiple biologic effects. Another endothelium-derived mediator nitric oxide (NO) is in contrast known to be potent vasorelaxing factor. Endothelin-1 (ET-1) is one of three recently identified potent vasoconstricting peptides which also include endothelin-2 and endothelin-3. The molecular structure and biological activities of endothelin were explored in several studies starting soon after its discovery in 1988, but only recently has the availability of specific ET-1 antagonists allowed its physiological activities to be explored.

There is now evidence that the excess production or excess secretion of endothelin is one of the factors responsible for e.g. systemic hypertension, pulmonary hypertension, pulmonary fibrosis, bronchial asthma, acute respiratory distress syndrome, myocardial infarction, thrombosis, congestive heart failure, cardiac hypertrophy, cerebral vasospasm, cerebral infarction, subarachnoidal haemorrhage, vascular dementia, Raynaud's disease, renal failure, cyclosporin nephrotoxicity, benign prostatic hyperplasia, diabetic angiopathy, gastric ulcer, liver cirrhosis, pancreatitis, migraine, glaucoma, retinopathy, sepsis, organ dysfunction after transplantation, multiple organ failure, preeclampsia and endotoxic shock.

Thus a compound which antagonizes endothelin or inhibits the production or secretion of endothelin has been considered to be useful in the treatment or prevention of the above various diseases.

Toremifene and tamoxifen are triphenylethylene antiestrogens currently used in the treatment of estrogen receptor positive breast cancer. The preparation of toremifene and its salts is described in U.S. Pat. No. 4,696,949. The use of toremifene for the reversal of multidrug resistance of cancer cells to cytotoxic compounds has been described in U.S. Pat. No. 4,990,538. The use of toremifene for treating autoimmune diseases has been described in WO 94/09764. The use of toremifene for sensitizing cancer cells to killer cell mediated lysis is described in WO 95/04544. Finally, the use of toremifene for lowering serum lipid peroxides has been described in WO 97/41847.

SUMMARY OF THE INVENTION

It has been found that toremifene or a pharmaceutically acceptable salt thereof is able to lower endothelin levels in mammals. Therefore toremifene or a pharmaceutically acceptable salt thereof is useful in the prevention or treatment of endothelin related conditions such as systemic hypertension, pulmonary hypertension, pulmonary fibrosis, bronchial asthma, acute respiratory distress syndrome, myocardial infarction, thrombosis, congestive heart failure, cardiac hypertrophy, cerebral vasospasm, cerebral infarction, subarachnoidal haemorrhage, vascular dementia, Raynaud's disease, renal failure, cyclosporin nephrotoxicity, benign prostatic hyperplasia, diabetic angiopathy, gastric ulcer, liver cirrhosis, pancreatitis, migraine, glaucoma, retinopathy, sepsis, organ dysfunction after transplantation, multiple organ failure, preeclampsia and endotoxic shock.

DETAILED DESCRIPTION OF THE INVENTION

In a first aspect the present invention provides a new medical use of toremifene or a pharmaceutically acceptable salt thereof in the manufacture of a medicament for use in lowering levels of endothelin in a patient.

The present invention also provides a new medical use of toremifene or a pharmaceutically acceptable salt thereof in the manufacture of a medicament for use in the prevention or treatment of endothelin mediated conditions. In particular the present invention provides a new medical use of toremifene or a pharmaceutically acceptable salt thereof in the manufacture of a medicament for use in the prevention or treatment of systemic hypertension, pulmonary hypertension, pulmonary fibrosis, bronchial asthma, acute respiratory distress syndrome, myocardial infarction, thrombosis, congestive heart failure, cardiac hypertrophy, cerebral vasospasm, cerebral infarction, subarachnoidal haemorrhage, vascular dementia, Raynaud's disease, renal failure, cyclosporin nephrotoxicity, benign prostatic hyperplasia, diabetic angiopathy, gastric ulcer, liver cirrhosis, pancreatitis, migraine, glaucoma, retinopathy, sepsis, organ dysfunction after transplantation, multiple organ failure, preeclampsia and endotoxic shock.

In another aspect the present invention provides a method for lowering endothelin levels in a patient comprising administering to a patient in need thereof an endothelin level lowering amount of toremifene or a pharmaceutically acceptable salt thereof.

In another aspect the present invention provides a method for the prevention or treatment of endothelin mediated conditions comprising administering to a patient in need thereof an endothelin lowering amount of toremifene or a pharmaceutically acceptable salt thereof. In particular, the present invention provides a method for the prevention or treatment of endothelin mediated conditions selected from a group consisting of systemic hypertension, pulmonary hypertension, pulmonary fibrosis, bronchial asthma, acute respiratory distress syndrome, myocardial infarction, thrombosis, congestive heart failure, cardiac hypertrophy, cerebral vasospasm, cerebral infarction, subarachnoidal haemorrhage, vascular dementia, Raynaud's disease, renal failure, cyclosporin nephrotoxicity, benign prostatic hyperplasia, diabetic angiopathy, gastric ulcer, liver cirrhosis, pancreatitis, migraine, glaucoma, retinopathy, sepsis, organ dysfunction after transplantation, multiple organ failure, preeclampsia and endotoxic shock.

Toremifene or a pharmaceutically acceptable salt thereof may be administered in a variety of ways including orally, parenterally or transdermally using conventional forms of preparations, such as capsules, tablets, granules, powders, suppositories, injections, patches, suspensions and syrups. The active compound may be administered monthly, weekly or daily or several times a day depending upon the patient's needs. A typical daily oral dosage is within the range of from about 1 mg to about 500 mg, preferably from about 5 to about 100 mg, of the active compound. However, the dosage may be properly varied depending on the age, body weight and conditions of the patient as well as on the administration method. The compound of the invention may be administered alone or together with other active compounds. The term "endothelin level lowering amount" means here an amount that is capable of lowering endothelin levels systemically, e.g. in plasma, or locally, e.g. in tissue.

The compositions according to the invention can be prepared by the methods commonly employed in the art. In addition to the active compound the compositions may contain pharmaceutically acceptable additives commonly used in the art, such as carriers, binders, excipients, lubricants, suspending agents and diluents. The amount of the active compound in the compositions of the invention is sufficient to produce the desired therapeutical effect, for example about 1 mg to 500 mg, more preferably from about 5 to about 100 mg, in unit dosage for both oral and parenteral administration.

Experiments

Effect of toremifene on endothelin-1 level in plasma

Postmenopausal breast cancer patients were treated with 40 mg/d toremifene (Fareston™) (n=19), 20 mg/d tamoxifen (Tadex™) (n=25) or 2 mg/d estradiol valerate (Progynova™)(n=14) orally for one year. The 44 patients of the antiestrogen groups had been operated on breast cancer 6–8 weeks before the trial. Plasma samples (10 ml) were collected before and at 6 and 12 months of each regimen, and plasma levels of endothelin-1 (ET-1) and nitrite/nitrate (NOx) were measured by established methods. The data (presented as mean±SE) were analyzed by two-way analysis of variance (ANOVA) for repeated measures. When differences were indicated by ANOVA, their significances at individual timepoints were calculated by means of a t-test for independent means (between-groups comparison) or a t-test for dependent means (comparison to baseline within a single group). For determination of correlation between two variables, the Pearsson coefficient was calculated. The results are shown in Table 1.

TABLE 1

Plasma levels of endothelin-1 (ng/l) and nitrite/nitrate ($\mu$mol/l) in breast cancer patients (ns = no significant).

|  | Before treatment | At 6 months | P (0–6) | At 12 months | P (0–12) |
| --- | --- | --- | --- | --- | --- |
| Endothelin-1 |  |  |  |  |  |
| Toremifene | 3.0 ± 0.2 | 2.6 ± 0.2 | 0.01 | 2.6 ± 0.2 | 0.06 |
| Tamoxifen | 3.5 ± 0.2 | 3.5 ± 0.2 | ns | 3.2 ± 0.2 | ns |
| Estrogen | 2.8 ± 0.2 | 2.7 ± 0.2 | ns | 2.7 ± 0.2 | ns |
| Nitrite/nitrate |  |  |  |  |  |
| Toremifene | 23.4 ± 4.0 | 21.0 ± 2.5 | ns | 21.6 ± 3.1 | ns |
| Tamoxifen | 20.6 ± 2.3 | 22.8 ± 4.0 | ns | 20.4 ± 2.5 | ns |
| Estrogen | 25.8 ± 3.7 | 21.5 ± 3.2 | ns | 18.5 ± 2.7 | ns |

The results show that toremifene significantly lowered endothelin-1 level in patients during the treatment whereas another antiestrogen tamoxifen had no effect. No treatment led to significant changes in plasma NOx.

Occurrence of thromboses and cerebrovascular accidents

In three clinical adjuvant trials effects of oral toremifene 40 mg/d was compared to oral tamoxifen 20 mg/day for 3 years in postmenopausal breast cancer patients. The occurrence of serious deep vein thromboses and serious cerebrovascular accidents in toremifen and tamoxifen groups are summarized in Table 2.

TABLE 2

The occurrence of deep vein thromboses and cerebrovascular accidents in clinical adjuvant trials in postmenopausal breast cancer patients.

|  | Toremifene | Tamoxifen |
| --- | --- | --- |
| Number of patients | 1120 | 1110 |
| Deep vein thromboses | 7 | 13 |
| Cerebrovascular accidents | 2 | 14 |

The results show that clearly more vascular complications (deep vein thrombosis and cerebrovascular events) are seen among tamoxifen treated patients than among those treated with toremifene. This difference may be explained by the beneficial effect of toremifene on endothelin-1 levels in the patients.

What is claimed is:

1. A method for lowering endothelin levels in a patient, comprising administering to the patient in need thereof an endothelin level lowering amount of toremifene or a pharmaceutically acceptable salt thereof.

2. A method for the prevention or treatment of endothelin mediated vasoconstriction or bronchoconstriction, comprising administering to a patient in need thereof an endothelin level lowering amount of toremifene or a pharmaceutically acceptable salt thereof.

3. A method according to claim 2, which further comprises the treatment or prevention of a condition selected from the group consisting of systemic hypertension, pulmonary hypertension, pulmonary fibrosis, bronchial asthma, acute respiratory distress syndrome, myocardial infarction, thrombosis, congestive heart failure, cardiac hypertrophy, cerebral vasospasm, cerebral infarction, subarachnoidal haemorrhage, vascular dementia, Raynaud's disease, renal failure, cyclosporin nephrotoxicity, benign prostatic hyperplasia, diabetic angiopathy, gastric ulcer, liver cirrhosis, pancreatitis, migraine, glaucoma, retinopathy, sepsis, organ dysfunction after transplantation, multiple organ failure, preeclampsia and endotoxic shock.

4. A method as claimed in claim 2, which comprises the treatment of endothelin mediated vasoconstriction or brochoconstriction.

5. A method as claimed in claim 3, which comprises the prevention of endothelin mediated vasoconstriction or brochoconstriction.

* * * * *

UNITED STATES PATENT AND TRADEMARK OFFICE
CERTIFICATE OF CORRECTION

PATENT NO.   : 6,569,904 B1
DATED        : May 27, 2003
INVENTOR(S)  : Olavi Ylikorkala et al.

It is certified that error appears in the above-identified patent and that said Letters Patent is hereby corrected as shown below:

<u>Title page,</u>
Item [57], ABSTRACT,
Lines 2-3, "phamaceutically" should read -- pharmaceutically --.
Line 3, "acceptable thereof" should read -- acceptable salt thereof --.

<u>Column 4,</u>
Lines 53-54, "brochoconstriction" should read -- bronchoconstriction --.
Lines 56-57, "brochoconstriction" should read -- bronchoconstriction --.

Signed and Sealed this

Fifteenth Day of July, 2003

JAMES E. ROGAN
*Director of the United States Patent and Trademark Office*